United States Patent
Camussi et al.

(10) Patent No.: US 11,395,832 B2
(45) Date of Patent: Jul. 26, 2022

(54) PHARMACEUTICAL CARRIERS CONTAINING MIRNAS FOR USE IN THE TREATMENT OF RENAL CANCER

(71) Applicant: UNICYTE EV AG, Oberdorf (CH)

(72) Inventors: Giovanni Camussi, Turin (IT); Benedetta Bussolati, Turin (IT); Tatiana Lopatina, Turin (IT)

(73) Assignee: UNICYTE EV AG, Oberdorf (CH)

( * ) Notice: Subject to any disclaimer, the term of this patent is extended or adjusted under 35 U.S.C. 154(b) by 16 days.

(21) Appl. No.: 16/772,280

(22) PCT Filed: Dec. 14, 2018

(86) PCT No.: PCT/EP2018/084907
§ 371 (c)(1),
(2) Date: Jun. 12, 2020

(87) PCT Pub. No.: WO2019/115748
PCT Pub. Date: Jun. 20, 2019

(65) Prior Publication Data
US 2021/0069231 A1    Mar. 11, 2021

(30) Foreign Application Priority Data
Dec. 14, 2017   (EP) .................................. 17207414

(51) Int. Cl.
*A61K 31/7105* (2006.01)
*C12N 15/113* (2010.01)
*C12Q 1/68* (2018.01)

(52) U.S. Cl.
CPC ........ *A61K 31/7105* (2013.01); *C12N 15/113* (2013.01); *C12N 2310/141* (2013.01); *C12N 2320/32* (2013.01)

(58) Field of Classification Search
None
See application file for complete search history.

(56) References Cited

U.S. PATENT DOCUMENTS

2020/0206285 A1* 7/2020 Finer .................... C12N 15/86
2021/0186877 A1* 6/2021 Shpall ................ C12N 15/1137

FOREIGN PATENT DOCUMENTS

| EP | 2363136 A1 | 9/2011 |
| EP | 2010663 B1 | 3/2015 |
| WO | 2005118806 A2 | 12/2005 |
| WO | 2006126219 A1 | 11/2006 |
| WO | 2006126236 A1 | 11/2006 |
| WO | 2009036236 A1 | 3/2009 |
| WO | 2009086156 A2 | 7/2009 |
| WO | 2011070001 A1 | 6/2011 |
| WO | 2011107437 A1 | 9/2011 |
| WO | 2017191234 A1 | 11/2017 |

OTHER PUBLICATIONS

Valentina Fonsato et al., Human Liver Stem Cell-Derived Microvesicles Inhibit Hepatoma Growth in SCID Mice by Delivering Antitumor MicroRNAs, Stem Cells, Sep. 20, 2012, vol. 30, Issue 9, pp. 1985-1998, AlphaMed Press.
Zhu Wei et al., Exosomes derived from human bone marrow mesenchymal stem cells promote tumor growth in vivo, Cancer letters, Feb. 2012, vol. 315, Issue 1, pp. 28-37, Elsevier.
Zhu Wei et al., Mesenchymal stem cells derived from bone marrow favor tumor cell growth in vivo, Experimental and Molecular Pathology, Jun. 2006, vol. 80, Issue 3, pp. 267-274, Elsevier.
Maria Beatriz Herrera et al., Isolation and Characterization of a Stem Cell Population from Adult Human Liver, Stem Cells, Dec. 2006, vol. 24, Issue 12, pp. 2840-2850, AlphaMed Press.
Benedetta Bussolati et al., Altered angiogenesis and survival in human tumor-derived endothelial cells, The FASEB Journal, (Published online Apr. 22, 2003), Jun. 2003, vol. 17, Issue 9, pp. 1159-1161, Federation of American Societies for Experimental Biology.
Maria Beatriz Herrera et al., Human liver stem cell-derived microvesicles accelerate hepatic regeneration in hepatectomized rats, Journal of Cellular and Molecular Medicine, Jun. 2010, vol. 14(6b), pp. 1605-1618, Foundation for Cellular and Molecular Medicine/Blackwell Publishing Ltd.
Pieter Mestdagh et al., A novel and universal method for microRNA RT-qPCR data normalization, Genome Biology 2009, vol. 10, Issue 6, Article R64, BioMed Central.
Ningning Yang, An overview of viral and nonviral delivery systems for microRNA, International Journal of Pharmaceutical Investigation, Oct. 2015, vol. 5, No. 4, pp. 179-181, Wolters Kluwer—Medknow Publications.
International Search Report, issued in PCT/EP2018/084907, dated Feb. 18, 2019, Rijswijk, Netherlands.
Zhang Wei et al. , MicroRNAs in Serum Exosomes as Potential Biomarkers in Clear-cell Renal Cell Carcinoma, European Urology Focus, Oct. 14, 2016, pp. 412-419, European Association of Urology, Elsevier B.V.

* cited by examiner

Primary Examiner — Sean McGarry
(74) Attorney, Agent, or Firm — Jacobson Holman PLLC (57) ABSTRACT

A method for treating renal cancer by administering a pharmaceutically acceptable carrier comprising a microRNA selected from the group consisting of miR-15a, miR-181b, miR-320c, miR-874 and any combination thereof is provided. In an embodiment, the pharmaceutically acceptable carrier is an extracellular vesicle (EV) derived from an adult stem cell selected from the group consisting of a mesenchymal stem cell (MSC), a non-oval human liver progenitor cell (HLSC) and an adipose stem cell (ASC).

8 Claims, 9 Drawing Sheets

PHARMACEUTICAL CARRIERS CONTAINING MIRNAS FOR USE IN THE TREATMENT OF RENAL CANCER

CROSS-REFERENCE TO RELATED APPLICATIONS

This application is a National Phase Application of PCT International Application No. PCT/EP2018/084907, having an International Filing Date of Dec. 14, 2018 claiming priority to European Patent Application No. 17207414.8, filed Dec. 14, 2017, each of which is hereby incorporated by reference in its entirety.

The present invention relates to a new therapeutic treatment of renal cancer. More in particular, the present invention relates to the use of pharmaceutical carriers carrying a specific set of miRNAs effective in the treatment of renal cancer. A focus lies on extracellular vesicles (EVs) derived from stem cells as the pharmaceutical carriers for the treatment of renal cancer.

Tumor vascularization is a fundamental step in tumor growth and metastasis. Solid tumors are in fact unable to grow over a few millimetres square in the absence of a vascular supply of oxygen and nutrients. Moreover, the number of metastases correlates to the vessel density of the primary tumor.

Tumor endothelial cells (TECs) are distinct from normal endothelial cells and display a pro-angiogenic phenotype. For instance, TECs demonstrate higher motility and proliferation, independency from serum in vitro and enhanced survival through Akt signaling. Phenotypically, TECs may have enhanced growth factor receptors expression, including VEGF and EGF receptors. TECs are also resistant to certain chemotherapeutic drugs and are less sensible to anti-angiogenic drugs targeting VEGF. Furthermore, TECs are genetically different from normal endothelial cells.

Extracellular vesicles (EVs) appear as an important mechanism of cell-to-cell communication, and their active cargo may reprogram recipient cells, by modifying their function and phenotype. In fact, the activity of EVs seems to relay on the transfer of a number of different factors, including proteins, RNAs, DNA and lipids, among which microRNAs appear to have a primary role. Stem cell derived EVs, and in particular human bone-marrow derived mesenchymal stromal cells (BM-MSCs) are known to display both pro-tumorigenic and anti-tumorigenic activities, depending on the tumor type and stage of development. Similarly, MSC-EVs may also positively or negatively modulate tumor vascularization (Zhu W, Huang L, Li Y, Zhang X, Gu J, Yan Y, et al. Exosomes derived from human bone marrow mesenchymal stem cells promote tumor growth in vivo. Cancer letters. 2012;315(1):28-37). MSC-EVs were reported to be pro-angiogenic in vivo after administration to tumor-bearing mice (Zhu W, Xu W, Jiang R, Qian H, Chen M, Hu J, et al. Mesenchymal stem cells derived from bone marrow favor tumor cell growth in vivo. Exp Mol Pathol. 2006;80(3):267-74). Other studies observed an indirect effect of MSC-EVs on VEGF secretion by tumor cells.

Recently, the present inventors have shown that another source of human resident non-oval multipotent progenitor cells expressing hepatic cell markers isolated from liver, i.e. human liver stem cells (HLSCs), may display anti-tumor effects (Herrera M B, Bruno S, Buttiglieri S, Tetta C, Gatti S, Deregibus M C, et al. Isolation and characterization of a stem cell population from adult human liver. Stem cells. 2006;24(12):2840-50). In particular, HLSC-EVs were shown to decrease hepatoma growth by a mechanism involving the delivery of specific antitumor miRNAs (Fonsato V, Collino F, Herrera M B, Cavallari C, Deregibus M C, Cisterna B, et al. Human liver stem cell-derived microvesicles inhibit hepatoma growth in SCID mice by delivering antitumor microRNAs. Stem cells. 2012;30(9):1985-98). However, whether HLSC-EVs also influence tumor angiogenesis was not investigated.

HLSC have been described in WO2006/126236.

Furthermore, to the inventors' knowledge, no antitumor effect of stem cell-derived EVs by the delivery of specific miRNAs has ever been reported against renal cancer.

WO 2011/107437 discloses that microvesicles derived from adult stem cells such as BM-MSCs, Gl-MSCs and HLSCs are effective in the treatment of tumor diseases such as liver, epithelial, lung, prostate, ovarian, breast, gastric and colon tumor. WO 2011/070001 discloses the use of HLSC-derived conditioned medium for the treatment of hepatoma, Kaposi's sarcoma and breast adenocarcinoma. Neither renal cancer nor the role of miRNAs are discussed in these patents.

As it will be illustrated in more detail in the experimental section of the present description, the inventors have now surprisingly found that extracellular vesicles (EVs) derived from adult stem cells, such as HLSC-EVs and MSC-EVs, are able to inhibit in vitro the migration of renal tumor endothelial cells, and that HLSC-EVs also significantly reduce vessel-like formation. In vivo experiments also showed that HLSC-EVs are able to inhibit tumor angiogenesis. Very interestingly, in these experiments HLSC-EVs did not show any effect on the normal endothelial cells. Accordingly, the present invention solves the problem of providing a product which is efficient in the therapeutic treatment of renal cancer.

EVs have a complex composition and contain a number of functional proteins, lipids and nucleic acids. The present inventors have identified four microRNAs carried by HLSC-EVs, namely miR-15a, miR-181b, miR-320c, and miR-874, which are able to inhibit tumor angiogenesis in vitro after renal cancer-TEC transfection. Transfection with these miRNAs led to the decreased expression of their target genes FGF1, PLAU, ITGB3, and EPHB4 respectively. When TECs were stimulated with EVs carrying the above-identified miRNAs, significant enhanced expression of the miRNAs was observed associated with inhibition of FGF1 and PLAU expression, whereas no inhibition of ITGB3 and EPHB4 was observed. FGF1 is the one of the most important pro-angiogenic factors involved in tumor angiogenesis and is able to regulate angiogenesis independently from VEGF. PLAU is a gene that codes urokinase-type plasminogen activator (uPA), an enzyme that activates plasmin from plasminogen. Plasmin participates in proteolytic processes of extracellular matrix degradation, which is important for angiogenesis and cancer progression. FGF1 and PLAU are colligated through receptors of FGF1 (FGFRs), which can activate uPA and enhance expression of its receptor uPAR. All of them, FGF1, uPA and uPAR, are linked in a positive feedback loop through FGFRs.

In light of these results, pharmaceutical carriers comprising miR-15a, miR-181b, miR-320c, miR-874 or mixtures thereof are very promising therapeutic agents for the treatment of renal cancer.

Therefore, a first aspect of the present invention is a pharmaceutically acceptable carrier comprising a microRNA selected from the group consisting of miR-15a, miR-181b, miR-320c, miR-874 and any combination thereof, for use in the treatment of renal cancer. According to a preferred embodiment of the invention, the pharmaceutically acceptable carrier comprises at least a combination of two of miR-15a, miR-181b, miR-320c and miR-874. Even more preferably the pharmaceutically acceptable carrier comprises all of miR-15a, miR-181b, miR-320c and miR-874.

miR-15a, miR-181b, miR-320c and miR-874 are microRNAs (miRNAs) known per se; their features and sequences may be found for example in the database designated as miR Base, under accession numbers MI0000069, MI0000269, MI0003778, MIPF0000401.

The pharmaceutical effect can be attributed to the miRNAs contained in the pharmaceutical carrier. Any efficient transfection of the target cell with miRNAs is envisioned for effective use in the treatment of renal cancer. An efficient transfection of miRNAs requires an appropriate pharmaceutical carrier, preferably in form of a micro- or nanoparticle. Such carriers are available commercially, including alginate-based (GEM, Global Cell Solutions), dextran-based (Cytodex, GE Healthcare), collagen-based (Cultispher, Percell), and polystyrene-based (SoloHill Engineering) microcarriers.

As an alternative, a pharmaceutical carrier for miRNAs may be a viral vector. Viral-based systems usually use retroviruses, lentiviruses, adenoviruses or adeno-associated viruses (AVV) as delivery vectors for, as disclosed for example in Ningning Yang. An overview of viral and nonviral delivery systems for microRNA. Int J Pharm Investig. 2015 October-December; 5(4): 179-181. Therefore, the selection and use of a suitable carrier for the miRNA is well within the capabilities of the person skilled in the art.

An even more preferred pharmaceutical carrier for miRNAs is a vesicle, such as a liposome or an extracellular vesicle (EV). Extracellular vesicles, such as cell derived microvesicles or exosomes are the most preferred pharmaceutical carriers.

Therefore, according to another preferred embodiment of the invention, the pharmaceutically acceptable carrier is an extracellular vesicle (EV) derived from a stem cell, preferably from an adult stem cell, more preferably from a mesenchymal stem cell (MSC), such as e.g. a bone marrow stromal stem cell, or from an adipose stem cell (ADS), or from a non-oval human liver progenitor cell (HLSC). HLSCs and methods of obtaining thereof are disclosed in International patent application published as WO2006126219.

A further aspect of the invention is a composition of extracellular vesicles isolated from the conditioned medium of a stem cell, preferably from the conditioned medium of an adult stem cell, more preferably from the conditioned medium of a mesenchymal stem cell (MSC) or a human liver stem cell (HLSC) or an adipose stem cell (ADS), for use in the treatment of renal cancer. Such extracellular vesicles are naïve, i.e. non-engineered EVs, isolated from the conditioned medium of a stem cell, which are effective in the therapeutic treatment of renal cancer by virtue of their intrinsic cargo of biologically-active molecules, particularly miRNAs.

Accordingly, the extracellular vesicle (EV) for use according to the invention is an isolated, naturally-occurring EV or, alternatively, an EV which has been engineered to contain one or more microRNAs selected from the group consisting of miR-15a, miR-181b, miR-320c, miR-874 and any combination thereof.

European patent application published as EP 2010663 provides the person skilled in the art with instructions on how to engineer EVs with specific miRNAs. Techniques known to the skilled person for introducing RNA into vesicles or exosomes are transfection or co-incubation. Known transfection methods are for example electroporation, lipofection, microinjection, transfection by viral and nonviral vectors, magnet assisted transfection and sonoporation. Consequently, an engineered EV to which a microRNA selected from the group consisting of miR-15a, miR-181b, miR-320c, miR-874 and any combination thereof has been introduced ex vivo is another aspect of the invention.

The engineered extracellular vesicle (EV) for use according the present invention contains an amount of the above-mentioned microRNA(s) which is significantly higher than the amount contained in the naturally-occurring extracellular vesicles (EVs).

The extracellular vesicle (EV) for use according the invention is a naturally occurring EV or, alternatively, an EV which has been engineered to contain a significantly higher amount of one or more microRNAs selected from the group consisting of miR-15a, miR-181b, miR-320c, miR-874 and any combination thereof compared to the naturally-occurring extracellular vesicle (EV). The engineered EV is obtainable by loading one or more microRNAs selected from the group consisting of miR-15a, miR-181b, miR-320c, miR-874 and any combination thereof to an isolated extracellular vesicle ex vivo. As an alternative, the engineered EV is obtainable by transfecting the miRNA(s) in a stem cell as defined above and then by isolating and purifying the EV from the conditioned medium of the transfected stem cell.

A suitable method to assess the significantly higher amount of miRNA(s) compared to the naturally-occurring extracellular vesicle (EV) is the AACT method of qPCR data analysis.

Expressed as a relative value, the loading efficiency, i.e. the amount of the target miRNA(s) which is present in the engineered EV of the invention as compared to the natural amount is of at least 2-fold. Alternatively, the loading efficiency may be expressed in absolute terms as the number of loaded target molecules per EV. It is envisaged that this value may range from about $1 \times 10^3$ to about $1 \times 10^5$ target molecules/EV higher that the natural amount.

The following experimental part, which discloses the experiments carried out by the inventors with EVs derived from MSCs and HLSCs, is provided by way of illustration only and is not intended to limit the scope of the invention as determined by the appended claims.

EXPERIMENTAL PART

Materials and Methods

Cell Cultures

TECs have been previously isolated and cultured in the inventors' laboratory from surgical specimens of patients with renal carcinomas 4. TEC were isolated from digested tissue using anti-CD105 positive selection by magnetic cell sorting (MACS system, Miltenyi Biotech, Auburn, Calif.) and grown in EndoGro complete medium (Millipore), as it was described (Bussolati B, Deambrosis I, Russo S, Deregibus M C, Camussi G. Altered angiogenesis and survival in human tumor-derived endothelial cells. FASEB journal, official publication of the Federation of American Societies for Experimental Biology. 2003;17(9):1159-61).

HLSCs were isolated in the inventors' laboratory from Human cryopreserved normal hepatocytes obtained from Lonza as it was described previously (Herrera M B, Bruno S, Buttiglieri S, Tetta C, Gatti S, Deregibus M C, et al. Isolation and characterization of a stem cell population from adult human liver. Stem cells. 2006;24(12):2840-50). Briefly, cells were plated hepatocyte serum-free medium (Gibco Hepatozyme-SFM; Invitrogen) at a density of 1.0–1.5×10$^5$ viable cells per cm$^2$ on collagen-coated culture plates for 2 weeks. After 2 weeks of culture, hepatocytes died, and then medium was substituted by α-minimum essential medium/endothelial cell basal medium-1 (α-MEM/EBM) (3:1) (Gibco/Euroclone) supplemented with L-glutamine (5 mM), Hepes (12 mM, pH7.4), penicillin (50 IU/ml), streptomycin (50 µg/ml), (all from Sigma), and 10% FBS (Lonza). Individual attached cells were cloned after 3 weeks and expanded. HLSCs are positive for CD73, CD90, CD29, and CD44 and negative for CD45, CD34, CD117 (c-kit), and CD133.

MSCs were purchased from Lonza and cultured in MSCBM complete medium (Lonza).

EV Isolation and Characterization

EV isolation was performed as it was described previously (Herrera M B, Fonsato V, Gatti S, Deregibus M C, Sordi A, Cantarella D, et al. Human liver stem cell-derived microvesicles accelerate hepatic regeneration in hepatectomized rats. Journal of cellular and molecular medicine. 2010;14(6B):1605-18) with minor modifications. Briefly, culture medium of confluent HLSC or MSC was changed on RPMI FBS free for 18 hours. Next day, this medium was centrifuged 30 minutes at 3000 g to remove cell debris and apoptotic bodies. After that supernatant was ultracentifuged 2 hours at 100.000 g, 4° C. using Beckman Coulter Optima L-100K Ultracetrifuge with the rotor type 45 Ti 45000 RPM. EV pellet was resuspended in RPMI supplemented with 10% of DMSO. Suspension of HLSC-EVs was then frozen at −80° C. until use. EVs were analysed using NTA analysis and electron microscopy. Mean size of EVs was 90 nm (±20). For some in vivo imaging experiments EV were labeled by 1 µM Vybrant Cell Tracers DiD (Ex: 640 nm; Em: 700 nm) or Dil solution without serum (Ex: 530 nm; Em: 580 nm) (Molecular Probes, Oregon, USA), then washed twice by ultracentrifugation in PBS 1X 40.

Viability and Migration Tests

For the test of proliferation, TECs were seeded in 96 well plate at the density 2×10$^3$/well. Next day, the cells were treated with HLSC-EVs or MSC-EVs in the concentrations 1×10$^{10}$ or 5×10$^{10}$ or 10×10$^{10}$EVs/TEC in EndoGro complete medium (Lonza). Proliferation was measured by BrdU incorporation at 24, 48 and 72 hours after EV stimulation using Cell Proliferation ELISA, BrdU (colorimetric) kit (Roche, 11647229001) according to manufacturer's instructions. Migration test was performed on TECs, seeded on 24-well plate and grown until confluence. EVs were added in the concentrations of 1×10$^{15}$ or 5×10$^{15}$ or 10×10$^{15}$EVs/well just after the scratch was done. Images on microscope with the magnificent 10× were done at time 0, 3, 7 and 24 hours after scratch. The distance was measured by LAS software (Leica). The results are presented as average radiance ±SD.

Vessel-Like Structure Formation in vitro

TECs were seeded onto Matrigel-coated 24-well plates at the density 25×10$^3$ cells per well and cultured in EndoGro complete medium in the presence of 1×10$^{10}$, 5×10$^{10}$, 10×10$^{10}$ or 20×10$^{10}$EVs/TEC. TECs without EVs were used as a control. After incubation for 24 h, phase-contrast images (magnification, ×10) were recorded and the total length of the network structures was measured using LAS software (Leica). The total length per field was calculated in five random fields and expressed as a ratio to the respective control. Data were expressed as average radiance ±SD.

In vivo Angiogenesis Model

Animal studies were conducted in accordance with the national guidelines and regulations and were approved by the Ethics Committee of the University of Torino (Protocol Number: 338/2016-PR). A model of in vivo tumor angiogenesis obtained by TEC injection within Matrigel was used to assess the effect of stem cell-derived EVs, as described (ref FASEB 2003). To prevent the development of tumor angiogenesis, TECs were pretreated before injection. For this purpose, SCID mice (6-8 weeks old) (Charles River Laboratories, Lyon, France) were subcutaneously injected with 1×10$^6$ TECs within Matrigel, pretreated or not with HLSC-EVs/MSC-EVs (10×10$^3$ EVs per cell): (n=8 for control, and each EV treatment). After 7 days, Matrigel plugs were excised and vessel density was analyzed by Masson's trichromic reaction. To evaluate the influence of EVs on established tumor vessels, 1×10$^6$ TECs were subcutaneously injected within Matrigel in SCID mice. HLSC-EVs (10×10$^3$ EV per cell) were injected twice into Matrigel plugs three days and seventh days after TEC injection. Control mice were injected with vehicle (PBS). At day 10 of the experiment, mice were sacrificed and Matrigel plugs were excised for the histochemical analysis (n=8 for control, and HLSC-EV treatment).

Biodistribution Analysis

For the in vivo imaging of EV uptake by TECs, twenty-five SCID mice were subcutaneously injected with 1×10$^6$ TEC within Matrigel. After tumor vessel development (1 week), mice were divided into five groups (n=5 each): CONTROL that received vehicle (PBS), DiL MSC-EVs, DiD MSC-EVs, DiL HLSC-EVs and DiD HLSC-EVs. DiD or DiL labeled EVs (1.3×10$^{10}$ EVs/mouse) were injected intravenously and mice were sacrificed after 5 hours. Organs obtained from mice treated with DiL EVs (Matrigel plug, skin, kidney, spleen, liver and lung) were recovered for immunofluorescence. Frozen sections of each organ were stained with Dapi for nuclear counterstaining and analyzed by confocal microscopy to detect DiL labeled EVs.

The bio-distribution of DiD-labeled EVs was evaluated by optical imaging. All the studies were performed with IVIS 200 small animal imaging system (PerkinElmer, Waltham, Mass.) using excitation filter at 640 nm and emission filter at 700 nm. Identical illumination settings, such as exposure time, binning factor, f/stop, and field of views (Grange 2014), were used for acquiring all images, and fluorescence emission was normalized to photons per second per centimeter squared per steradian (p/sec/cm$^2$/sr). Images were acquired on organs collected 5 hours after EV injection. To control for the background photon emission, the obtained data were subjected to average background subtraction, using data captured with an excitation of 535 nm. Images were acquired and analyzed using Living Image 4.0 software (PerkinElmer) (Grange 2014). The fluorescence (p/sec/cm$^2$/sr) was quantified in region of interest (ROI) draw freehand. Data were expressed as average radiance ±SD.

Gene Expression Study and Real-Time PCR miRNA expression levels in HLSC-EVs or MSC-EVs were analysed using the Applied Biosystems TaqMan® Array Human MicroRNA A/B Cards (Applied Biosystems, Foster City, Calif.) to profile 754 mature miRNAs by qRT-PCR. The kit used microRNA-specific stem-loop reverse transcription primers and TaqMan probes to detect mature miRNA transcripts in a 2-step real-time reverse-transcription PCR assay. Briefly, single stranded cDNA was generated from total RNA sample (80 ng) by reverse transcription using a mixture of looped primers (Multiplex RT kit, Applied Biosystems) following manufacturer's protocol. The RT reactions were then diluted and mixed with a Taqman universal master Mix (Applied) in a ratio 1:1, loaded in the TaqMan microfluid card and qRT-PCR experiments were performed. All reactions were performed using an Applied Biosystems 7900HT real-time PCR instrument equipped with a 384 well reaction plate. Raw Ct values were calculated using the SDS software version 2.3 using automatic baseline and threshold. We have analyzed miR expression in 3 samples of HLSC-EVs. All microRNAs that were amplified after 35 cycles of PCR were classified as non-expressed. Only microRNA that were detected or not in more than two samples were taken under consideration. qRT-PCR was used to confirm miRNAs or target gene expression in TEC. Briefly, 200 ng of input RNA from all samples were reverse transcribed with the miScript Reverse Transcription Kit and the cDNA was then used to detect and quantify miRNAs or gene of interest by qRT-PCR using the miScript SYBR Green PCR Kit (all from Qiagen, Valencia, Calif., USA). All samples were run in triplicate using 3 ng of cDNA for each reaction as described by the manufacturer's protocol (Qiagen). Relative expression data were then normalized using the mean expression value, calculated on the overall miRNA expression in each array, according to a Ct detection cut-off of 35 PCR cycles as described in Mestdagh P, Van Vlierberghe P, De Weer A, Muth D, Westermann F, Speleman F, et al. A novel and universal method for microRNA RT-qPCR data normalization. Genome biology. 2009;10(6):R64). PCR analysis of the pro-angiogenic gene expression in TECs, treated or not with HLSC-EVs, was performed using Human Angiogenesis PCR Array (RT2 Profiler PCR array, 96/well Format, Qiagen) in triplicate according to manufacturer's instructions. Data were analyzed using the SaBioscience (Qiagen) on line software and expressed as Relative Quantification±CI (Confidence interval).

Cell Transfection

Transfection of TECs was performed using HiPerfect reagent (Qiagen). To find the optimal transfection concentrations, TECs were transfected with all recommended concentrations of mimic miR-FITC and HiPerfect reagent. Double augmentation of the maximum dose of HiPerfect (9 µl of HiPerfect per $50 \times 10^3$ TECs) was performed as well. FACS analysis, performed the day after transfection, revealed that double maximum dose of the HiPerfect permitted to transfect more than 60% of TECs with no damage on their viability and proliferation. This dose was used for all transfection experiments.

Transfection of TECs was performed using following mimic miRNAs: miR-15a, miR-20b, miR-23a, miR-93, miR-181b, miR-320c, miR-424, and miR-874 (all from Qiagen). Theay after transfection fresh growth medium was replaced and at day 2 the cells were used for the in vitro experiments (proliferation, apoptosis tests, angiogenesis in vitro assay) or gene expression analysis (Real time PCR, Western blot, FACS analysis).

Fluorescence-Activated Cell Sorting (FACS) Analysis

FACS analysis of HLSC-EVs and MSC-EVs was performed using CytoFLEX Flow Cytometer (Beckman Coulter). Antibody used were the FITC-conjugated antibodies anti CD63 (Abnova), anti CD105 (Dako Cytomation, Copenhagen, Denmark), anti CD90 (BD Pharmigen), anti CD44 (Miltenyi Biotech), CD45 (BD Pharmigen), anti ICAM and anti VCAM (Serotec), CD31 (BioLegend), integrin subunit α4, α5, α6 (from BD Pharmigen); PE-conjugated antibodies anti-CD73 (BD Pharmigen), anti integrin subunit α4, α5 (all from BD Pharmigen) and VE-cadherin (BioLegend). FITC or PE mouse non-immune isotypic IgG (Dako Cytomation) was used as control.

Western Blot

Protein samples were separated by 4% to 15% gradient sodium dodecyl sulfate-polyacrylamide gel electrophoresis (SDS PAGE) and subjected to immunoblotting with antibodies to PLAU (Abcam, ab131433) or FGF1 (Abcam ab9588). The protein bands were visualized with an enhanced chemiluminescence (ECL) detection kit and ChemiDoc™ XRS+ System (BioRad). Twenty µg/well of cell lysates were loaded.

Statistics

Data were assessed for normality of distribution using the Kolmogorov-Smirnov test. Statistical analysis was performed using SigmaPlot 11.0 Software. Differences between treatment and control groups were then analyzed using Student t-test when the distribution was normal. Data are expressed as mean±SEM. Differences were considered to be significant when $p<0.05$.

Results

HLSC-EVs Inhibit Angiogenic Potential and Migration of Renal TEC in vitro

Figure 1:
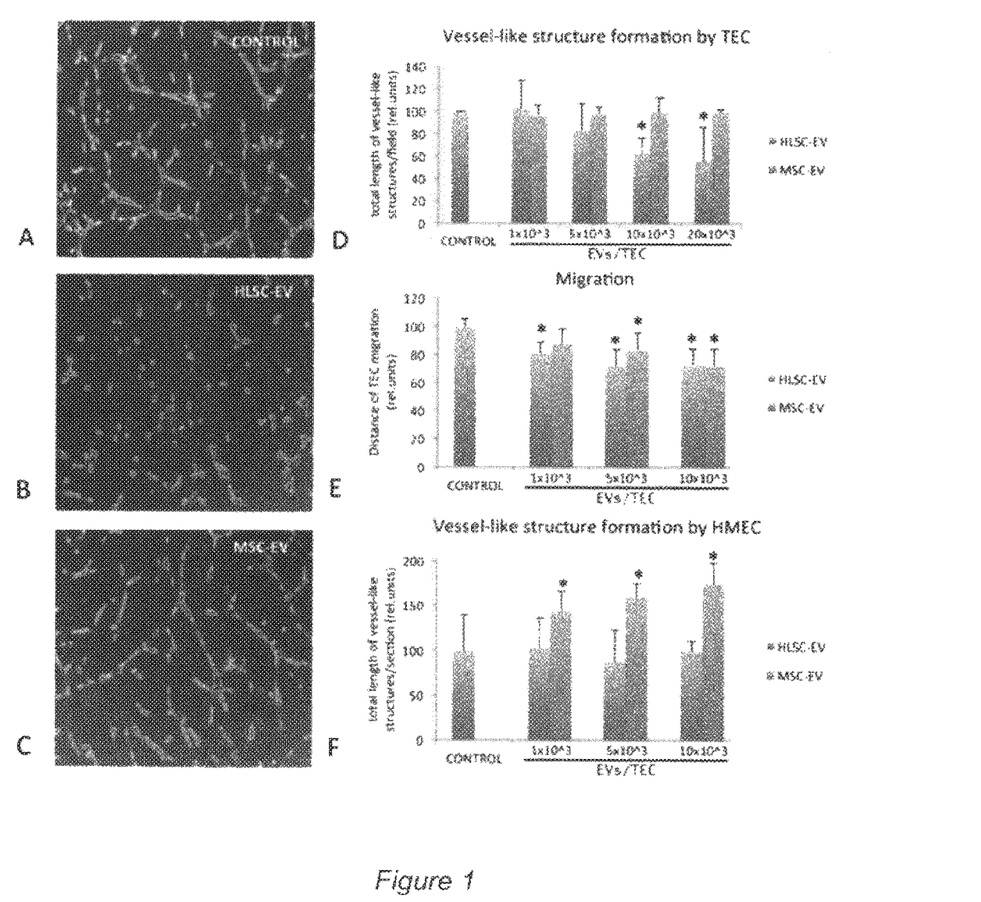

The influence of MSCEVs and HLSC-EVs on TECs by in vitro evaluation of proliferation, apoptosis and vessel-like structure formation was assessed. HLSC-EV stimulation significantly inhibited TEC angiogenesis in vitro at dose-depended manner: the addition of $10 \times 10^3$ EVs per TEC decreased vessel-like structure formation by 37% and a dose of $20 \times 10^3$ EV per TEC decreased vessel-like structure formation by 44% (FIG. 1, A, B, D). Both MSCEVs and HLSC-EVs did not change the viability of TECs (data not shown). The effect of MSC-EVs and HLSC-EVs on TEC motility was also evaluated by wound healing assay. Both EVs significantly inhibited the migration of TECs, and HLSC-EVs were already effective at the dose of $1 \times 10^3$ per TEC (FIG. 1, E).

In control experiments, the effect of MSC-EVs and HLSC-EVs was evaluated on normal endothelial cells: MSC-EVs were able to enhance the angiogenic property of human microvascular endothelial cells (HMECs), whereas HLSC-EV did not show any effect (FIG. 1, F). This indicates that EVs from MSC and HLSC have different action on normal and tumor angiogenesis.

FIG. 1. Effect of HLSC-EV or MSC-EV on angiogenic properties of TECs in vitro. Formation of vessel-like structure by control TECs (A), by TECs treated with HLSC-EVs (B) and by TECs treated with MSC-EVs (C); diagram of the total length of vessel-like structures per field, formed by control TEC or treated with EVs (D); diagram of the TEC migration during wound healing assay (E); diagram of the total length of vessel-like structures per field, formed by HMEC, treated with EVs (F).

HLSC-EVs Prevent Tumor Angiogenesis in vivo

Figure 2:
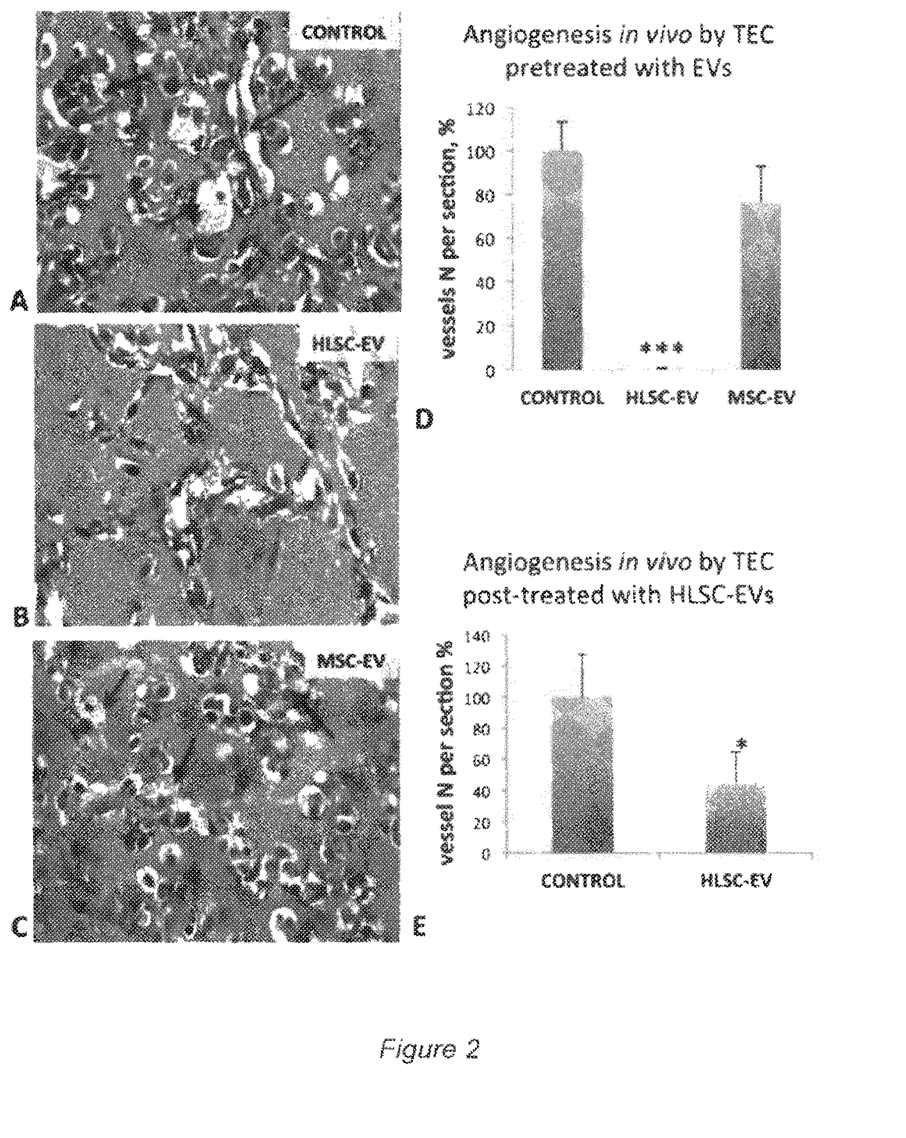

The effect of MSC-EVs and HLSC-EVs was evaluated in vivo by using a model of human tumor angiogenesis induced by TEC organization within Matrigel when implanted subcutaneously in SCID mice. In this model, TECs organize in tructures connected with the mouse circulation within 7 days. In a pre-treatment setting, TECs were treated with HLSC-EVs or MSC-EVs for 24 hours and implanted subcutaneously into SCID mice. Seven days after implantation, Matrigel plugs were excised and vessel density analyzed immunohistochemically. The analysis of control plugs showed, as expected, the presence of vessels connected with the murine vasculature (FIG. 2, A). Plugs of TECs treated with HLSC-EVs for 24 hours before implantation did not present erythrocytes containing vessels (FIG. 2 B, D), whereas pretreatment with MSC-EVs did not show any effect (FIG. 2 C, D).

Since HLSC-EVs were able to prevent tumor angiogenesis, their effect on established tumor vessels was also evaluated. For this aim, HLSC-EVs were injected into Matrigel plugs 3 and 7 days after TEC implantation and plugs were recovered after 10 days. HLSC-EV treatment significantly reduced vessel density of almost 50% (FIG. 2, E).

FIG. 2. Tumor angiogenesis in vivo. Representative images of Matrigel sections, stained with Masson's trichromic reaction (extracellular matrix is stained in blue, cells in red and erythrocytes in yellow): A—Matrigel plugs contained control TECs, B—Matrigel plugs contained TECs treated with HLSC-EVs, C—Matrigel plugs contained TECs treated with MSC-EVs. Erythrocytes containing vessels are indicated by arrows. D—diagram of vessel density in Matrigel contained control or pre-treated with EVs TEC (n=8, 5 fields/experiment were analyzed, ***–p<0,001 vs. control TEC). E—diagram of vessel density in TEC contained Matrigel, treated or not with HLSCEVs on the third and seventh days after injection (n=8, 5 fields/experiment were analyzed, *–p<0,05 vs. control Matrigel).

In vivo Up-Take of HLSC-EVs into TECs

Figure 3:
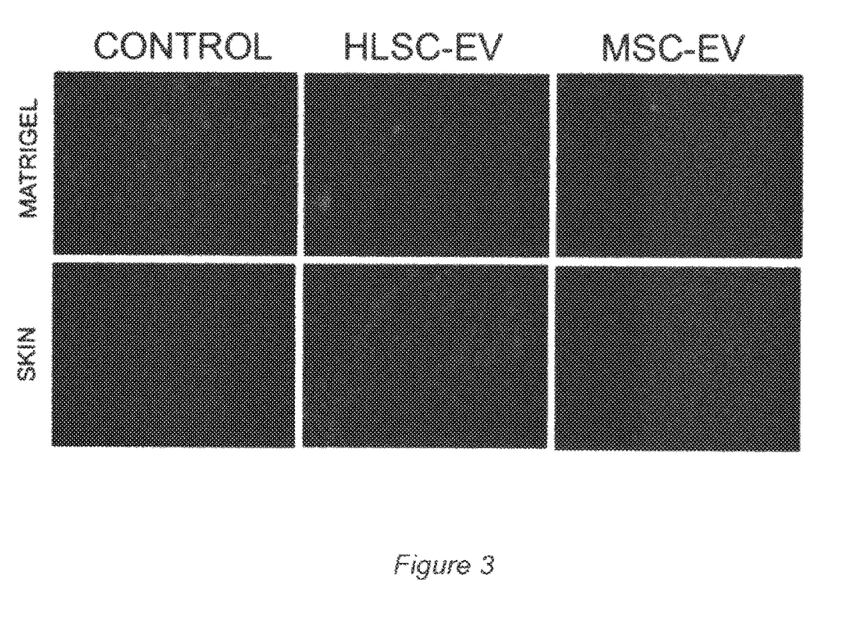

In order to evaluate the in vivo the ability of TECs, already organized into vessels, to uptake EVs, labeled MSC-EVs and HLSC-EVs ($1.3 \times 10^{10}$ EVs/mouse) were injected intravenously. EVs were labeled with fluorescent dyes, near red (DiD) for optical imaging and red (DiL) for immunofluorescence (see methods). After five hours, mice were sacrificed and organs were recovered. Dose of EVs and time were selected based on preliminary experiments (not shown). By Optical Imaging, we demonstrated that TECs injected in vivo within Matrigel could up-take both types of DiD labeled EVs (MSC-EVs and HLSC-EVs) as shown in FIGS. 3A and C. On the contrary, dermal tissue isolated in the proximity of the plug generated a very low fluorescence signal (FIGS. 3B and C). Regarding biodistribution within all organs, EVs mainly accumulated within liver.

FIG. 3. Biodistribution of labeled EVs. A and B. Representative images by Optical Imaging of Matrigel plugs (A) and explanted organs (B) collected 5 hours post EV injection. CTL: untreated; MSC-EV: treated with DiD MSC-EVs; HLSC-EV: treated with DiD HLSC-EVs. C. Quantification of fluorescence intensity of Matrigel plug and adjacent skin expressed as Average Radiance±SD at 5h after sacrifice of mice treated with DiD MSC-EVs and DiD HLSC-EVs. Background derived from of untreated mouse was subtracted (N=5). D. Quantification of fluorescence intensity of organs (lung, liver, spleen and kidney) expressed as Average Radiance ±SD at 5h after sacrifice of mice treated with DiD MSC-EVs and DiD HLSC-EVs. Background derived from of untreated mouse was subtracted (N=5).

Figure 4:
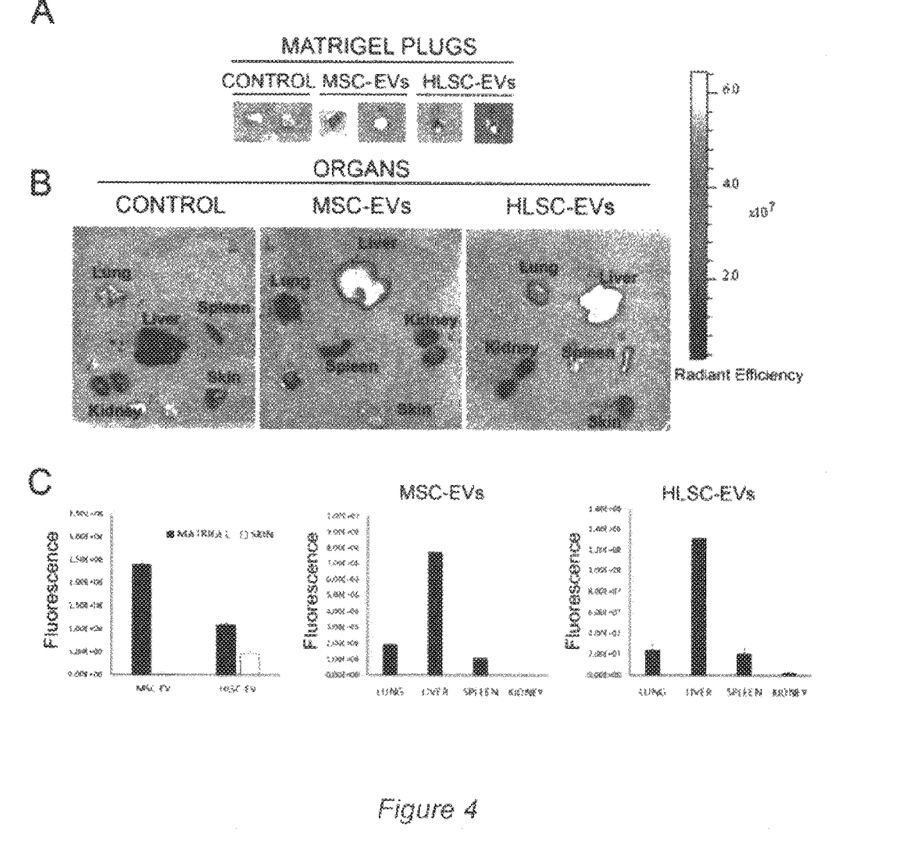

Similar results were obtained by immunofluorescence on explanted organs. In Matrigel plugs, DiL labeled EVs, both shed by MSCs and HLSCs were detectable within human TECs by confocal analysis (FIG. 4, A). The accumulation is rather specific for TECs as compared to normal endothelial cells in skin (FIG. 4, A). This confirms that TECs were able to uptake EVs within Matrigel. By immunofluorescence, EVs were also visible within liver parenchyma and spleen of all samples (FIG. 4, B). Few positive cells were present in lungs and kidneys. No differences were observed for biodistribution of EVs shed by MSCs compared with HLSCs.

FIG. 4. Detection of labeled DiL EVs in tissues. Representative fluorescence images of Matrigel plug and skin (A) and other organs (liver, spleen, kidney and lung) of mice, 5 hours after intravenous injection of MSC- or HLSC-labelled EVs. DiL EVs (red spots) are detectable within cells in Matrigel and excretory organs. Nuclei are co-stained with DAPI (blue) (N=5).

Molecular Effects of HLSC-EVs on TECs

Figure 5:
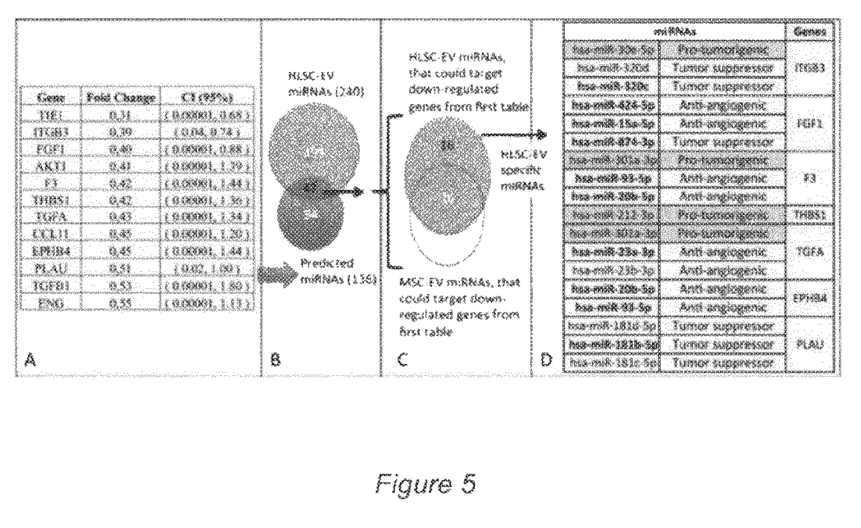

Based on these results, a molecular analysis of changes occurring in TECs after HLSC-EV stimulation during the in vitro vessel-like structure organization was performed by using a Angiogenesis array. TECs were treated with HLSC-EVs ($10 \times 10^3$ EVs/TEC) and spreading cells from angiogenesis assays were harvested. Among the 84 genes tested, we identified 11 pro-angiogenic factors significantly downregulated in TECs by HLSC-EVs during angiogenesis in vitro (FIG. 5, A). In particular, TECs downregulated pro-angiogenic surface receptors including Tie-1, beta 3 integrin (ITGB3), ephrin receptor B4 (EPHB4) and endoglin (or CD105)); as well as growth factors such as FGF1, TGF family members, urokinase-type plasminogen activator (PLAU) and tissue factor (F3). Finally Akt1, known to be involved in the pro-angiogenic effects of TECs, was also downregulated.

FIG. 5. Selection of HLSC-EV specific miRNAs, responsible for anti-angiogenic effect on TEC. A—List of the genes down-regulated in TEC after treatment with HLSC-EVs (n=3, data present as average Fold change±CI (Confidence interval); these genes could be targeted by 136 miRNAs (B), 42 of which are carried by HLSC-EVs. Form these 42 miRNAs 26 are also carried by MSC-EVs, which did not show any anti-tumor effect on TEC, therefore these 26 miRNAs were excluded from the study (C). Sixteen HLSC-EV specific miRNAs that could be relevant for EV biologic action on TEC. miRNAs selected for the study are in bold.

Identification of Anti-Angiogenic MicroRNAs Carried by HLSC-EVs

Subsequently, in order to dissect the possible effectors of the observed gene regulation, the microRNA content of HLSCs possibly involved was studied. For this aim, a strategy of bioinformatics analysis was used, followed by in vitro functional validation.

Using the Funrich V3 software, the inventors predicted miRNAs that target the 11 down-regulated genes. 136 miRNAs were identified and matched with miRNAs carried by HLSC-EVs (data base deposed on vesiclepedia). Among them, 42 miRNAs expressed by HLSC-EVs were identified (FIG. 5, B). A subsequent analysis excluded, among the 42 miRNAs carried by HLSC-EV, those also present in MSC-EVs, in consideration of the lack of effect on TECs (FIG. 5, C). Sixteen miRNAs targeting the identified genes were present only in HLSC-EVs and were used for the functional studies. (FIG. 5, D). Among them, three were described as pro-tumorigenic (hasmiR-30e-5p, has-miR-301a-3p, has-miR-212-3p), and three (miR-23, miR-181, miR-320) were present with more than one member of miRNA family Therefore, the inventors took in consideration 8 miRNAs: miR-15a, miR-20b, miR-23a, miR-93, miR-181b, miR-320c, miR-424, and miR-874 (FIG. 5, D, in bold). Interestingly, these selected miRNAs were down-regulated in the control TEC (Ct>33).

Effect of HLSC-EV miRNAs on TEC Angiogenesis

Figure 6:
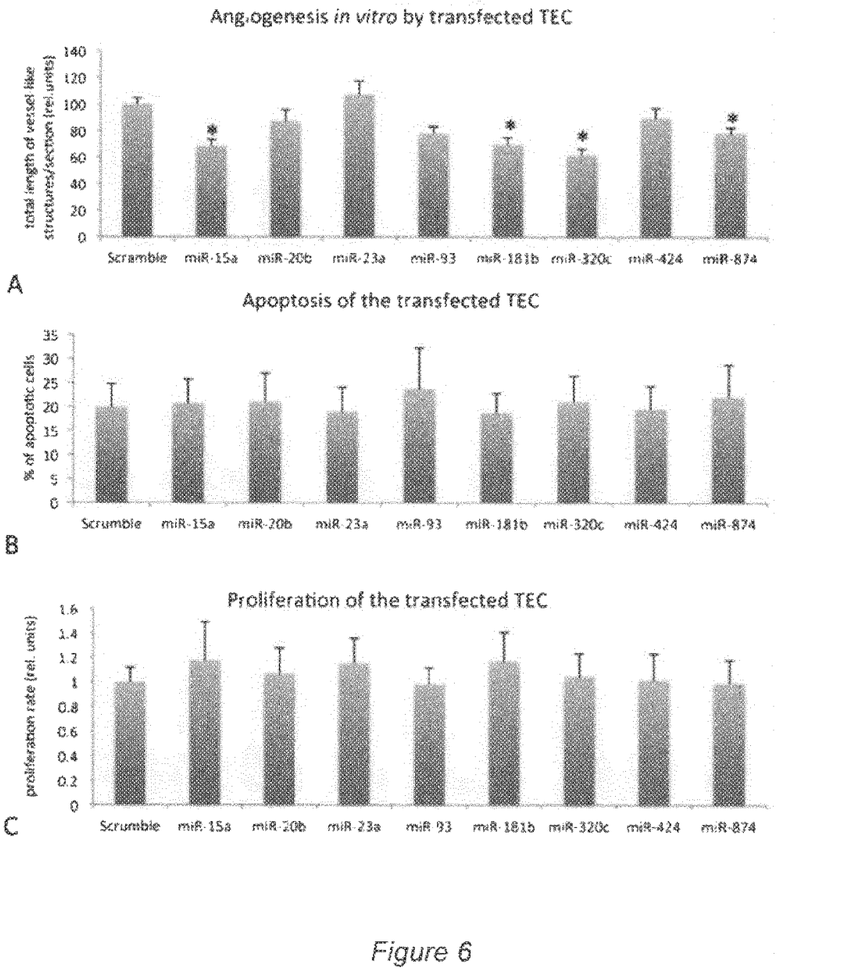

To demonstrate the specific effect of these separate miRNAs on TEC angiogenic properties, TECs were transfected with the selected mimics. Two days after transfection a vessel-like structure formation in vitro assay was performed. Four miRNAs significantly inhibited in vitro vessel-like structure formation: miR-15a, miR-181b, miR-320c and miR-874 (FIG. 6, A). No effect of mimics was observed on proliferation or apoptosis (FIGS. 6, B and C).

FIG. 6. Influence of the selected HLSC-EV specific miRNAs on pro-angiogenic properties and viability of TEC. A—diagram of vessel-like structure formation in vitro by TEC transfected with selected mimic-RNA or scramble RNA. (n=3, in duplicates, 10 images for well, *–p<0,05 vs. scramble); B—apoptosis rate of the transfected TEC; C—proliferation rate of the transfected TEC.

Therefore, the inventors investigated how transfection with the four active miRNA mimics changed the expression of the predicted targets (EPHB4, ITGB3, FGF1, and PLAU). TEC transfection significantly down-regulated their targets (Table 1, FIG. 7).

TABLE 1

Relative expression of pro-angiogenic genes in TECs, transfected with the selected miRNAs, versus control TECs.

| Gene | RQ in transfected TECs vs. control TECs |
|---|---|
| ITGB3 | 0.33 (miR-320c) |
| FGF1 | 0.39 (miR-15a) |
| EPHB4 | 0.39 (miR-181b) |
|  | 0.48 (miR-874) |
| PLAU | 0.51 (miR-181b) |

Figure 7:
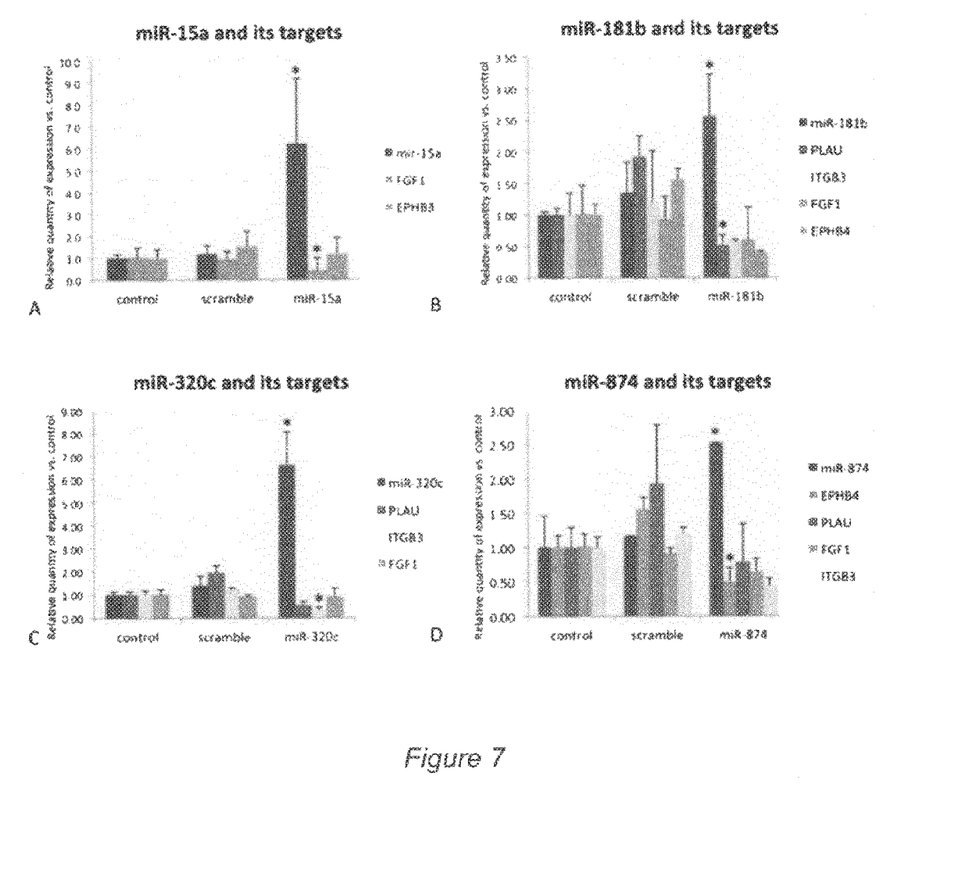

FIG. 7. Expression of miRNAs and their targets in TECs transfected with the selected mimic miRNAs. A—expression of miR-15a and its target genes FGF1, EPHB4; B—expression of miR-181b and its target genes PLAU, ITGB3, FGF1, EPHB4; C—expression of miR-320c and its target genes PLAU, ITGB4, FGF1; D—expression of miR-874 and its target genes EPHB4, PLAU, ITGB3, FGF1; (n=5, *–p<0,05 vs. scramble).

The expression of these miRNAs was found to be significantly enhanced in TECs treated with HLSC-EVs (FIG. 8, A), indicating the validity of the in silico data. In parallel, the effect of HLSC-EVs on the four target genes of the mimics (EPHB4, ITGB3, FGF1, and PLAU) was evaluated at both RNA and protein level.

Figure 8:
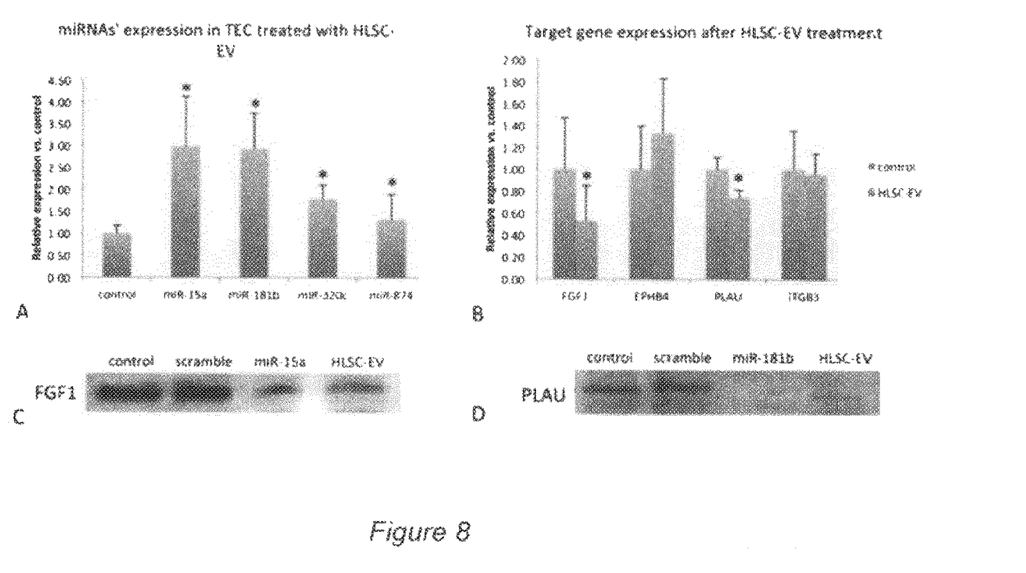

FIG. 8. Expression of miRNAs and their targets in TECs treated with HLSC-EV. A—relative expression of miRNAs in the control TECs and TECs treated with HLSC-EVs (n=7, *–p<0,05 vs. control); B—relative expression target genes in control TECs and TECs treated with HLSC-EVs (n=7, *–p<0,05 vs. control); C—representative image of Western blot analysis of the FGF1 expression in control TECs, TECs transfected with miR-15a or stimulated with HLSC-EVs. D—representative image of Western blot analysis of the PLAU expression in control TECs, TECs transfected with miR-181b or stimulated with HLSC-EVs.

Two targets, namely FGF1 and PLAU, were confirmed to be significantly reduced in cells treated with HLSC-EVs in normal culture conditions (FIG. 8, B). The down-regulation of FGF1 and PLAU expression in transfected TECs or TECs treated with HLSC-EVs was confirmed by Western blot (FIGS. 8, C and D respectively).

Transfection of Tumor Endothelial Cells with Combinations of miRNAs and Evaluation of Anti-Angiogenic Effect TECs were transfected using HiPerfect reagent (Qiagen) using the following combinations of miRNAs: miR-874/miR-15a; miR-874/miR-181b; miR-847/miR-320c; and miR181c/miR-320. Two days after transfection, an angiogenesis in vitro assay was performed. All combinations of miRNAs significantly reduced pro-angiogenic properties of TECs. Moreover, the combinations of miRNAs were more effective than single miRNAs.

Figure 9:
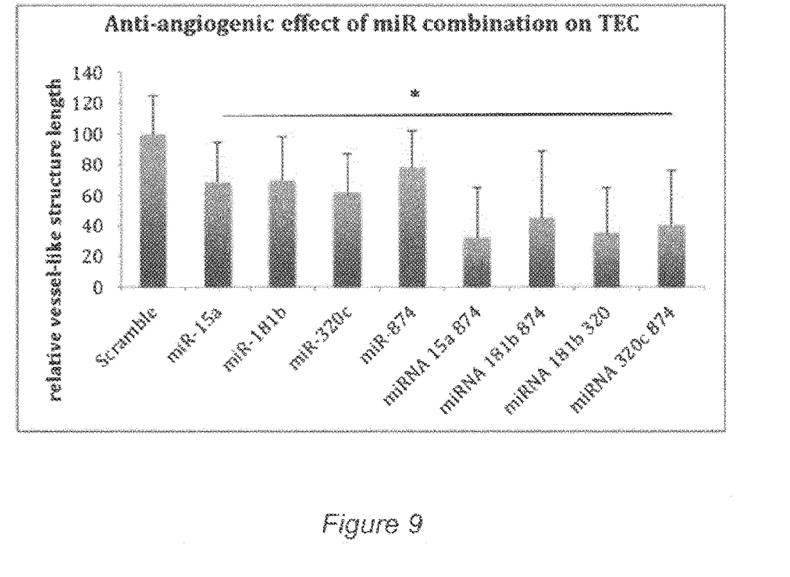

The results are reported in FIG. 9, which is a bar graph showing the relative quantity of vessel-like structures formed by TECs transfected with single or combined miRNAs. (*=p<0.01 vs. scramble).

The invention claimed is:

1. A method for treating renal cancer, the method comprising administering to a person in need thereof, a pharmaceutically acceptable carrier comprising a microRNA selected from the group consisting of miR-15a, miR-181b, miR-320c, miR-874 and any combination thereof.

2. The method of claim 1, wherein the pharmaceutically acceptable carrier comprises a combination of at least two microRNAs selected from the group consisting of miR-15 a, miR-181b, miR-320c and miR-874.

3. The method of claim 1, wherein the pharmaceutically acceptable carrier is a micro- or nanoparticle and wherein the microRNA or microRNAs is/are contained inside the micro- or nanoparticle or is/are attached to a surface of the micro- or nanoparticle.

4. The method of claim 1, wherein the pharmaceutically acceptable carrier is an extracellular vesicle (EV).

5. The method of claim 4, wherein the extracellular vesicle (EV) is derived from a stem cell.

6. The method of claim 5, wherein the extracellular vesicle (EV) is derived from an adult stem cell.

7. The method of claim 6, wherein the extracellular vesicle (EV) is derived from an adult stem cell selected from the group consisting of a mesenchymal stem cell (MSC), a non-oval human liver progenitor cell (HLSC) and an adipose stem cell (ASC).

8. The method of claim 4, wherein the extracellular vesicle (EV) is engineered to contain a microRNA selected from the group consisting of miR-15a, miR-181b, miR-320c, miR-874 and any combination thereof.

* * * * *